US009487632B2

(12) United States Patent
Männle et al.

(10) Patent No.: US 9,487,632 B2
(45) Date of Patent: Nov. 8, 2016

(54) METHOD FOR THE MANUFACTURE OF POLYBRANCHED ORGANIC/INORGANIC HYBRID POLYMERS

(71) Applicant: SINVENT AS, Trondheim (NO)

(72) Inventors: Ferdinand Männle, Oslo (NO); Christian Simon, Oslo (NO); Jest Beylich, Oslo (NO); Keith Redford, Hagan (NO); Britt Sommer, Oslo (NO); Einar Hinrichsen, Borgen (NO); Erik Andressen, Oslo (NO); Kjell Olafsen, Oslo (NO); Terje Didriksen, Oslo (NO)

(73) Assignee: Sinvent AS, Trondheim (NO)

( * ) Notice: Subject to any disclaimer, the term of this patent is extended or adjusted under 35 U.S.C. 154(b) by 0 days.

(21) Appl. No.: 14/330,271

(22) Filed: Jul. 14, 2014

(65) Prior Publication Data
US 2014/0323752 A1   Oct. 30, 2014

Related U.S. Application Data

(62) Division of application No. 11/578,470, filed as application No. PCT/NO2005/000126 on Apr. 15, 2005, now Pat. No. 8,802,807.

(30) Foreign Application Priority Data

Apr. 15, 2004   (NO) .................................. 20041546

(51) Int. Cl.
C08G 77/26    (2006.01)
C08G 83/00    (2006.01)
C08G 77/388   (2006.01)
C08G 77/54    (2006.01)
C07F 7/10     (2006.01)

(52) U.S. Cl.
CPC ............. *C08G 83/005* (2013.01); *C07F 7/10* (2013.01); *C08G 77/388* (2013.01); *C08G 77/54* (2013.01)

(58) Field of Classification Search
CPC .............................. C07F 7/10; C08G 77/388
See application file for complete search history.

(56) References Cited

U.S. PATENT DOCUMENTS

| | | | |
|---|---|---|---|
| 3,734,763 A | 5/1973 | Plueddemann | |
| 4,772,716 A | 9/1988 | Mulhaupt et al. | |
| 5,096,942 A | 3/1992 | Long et al. | |
| 5,110,863 A | 5/1992 | Sugama | |
| 5,494,949 A | 2/1996 | Kinkel et al. | |
| 5,674,941 A | 10/1997 | Cho et al. | |
| 5,744,243 A | 4/1998 | Li et al. | |
| 6,103,848 A | 8/2000 | Decker et al. | |
| 6,248,682 B1 | 6/2001 | Thompson et al. | |
| 6,395,867 B1 | 5/2002 | Maignan | |
| 6,479,057 B2 | 11/2002 | Allwohn et al. | |
| 6,663,952 B1 | 12/2003 | Mehnert et al. | |
| 6,750,270 B1 | 6/2004 | Klostermann et al. | |
| 2003/0055193 A1 | 3/2003 | Lichtenhan et al. | |
| 2004/0120915 A1 | 6/2004 | Yang et al. | |

FOREIGN PATENT DOCUMENTS

| | | |
|---|---|---|
| DE | 2 023 968 | 2/1971 |
| DE | 2023 968 | 2/1971 |
| DE | 199 33 098 A1 | 1/2001 |
| EP | 0 253 770 A1 | 7/1986 |
| EP | 0 253 770 A1 | 1/1988 |
| EP | 0 486 469 A1 | 5/1992 |
| EP | 0 666 290 A1 | 8/1995 |
| EP | 0 786 499 A1 | 7/1997 |
| EP | 0 972 788 A2 | 1/2000 |
| FR | 2 761 691 A1 | 4/1997 |
| FR | 2 761 691 A1 | 10/1998 |
| GB | 1 306 992 | 2/1973 |
| JP | 56 156290 | 12/1981 |
| JP | 06 128379 | 5/1994 |
| JP | 2001-192485 A | 7/2001 |
| SE | 9603174 | 3/1998 |
| WO | 94/07948 A1 | 4/1994 |
| WO | WO 94/07948 A1 | 4/1994 |
| WO | 97/19987 A1 | 5/1997 |
| WO | 00/22039 A1 | 4/2000 |
| WO | WO 00/22039 A1 | 4/2000 |
| WO | 01/10871 A1 | 2/2001 |
| WO | 01/48057 A1 | 7/2001 |
| WO | 02/08343 A2 | 1/2002 |
| WO | 02/092668 A1 | 11/2002 |
| WO | 03/029361 A2 | 4/2003 |
| WO | WO 03/029361 A2 | 4/2003 |

OTHER PUBLICATIONS

Gravel (Applied Organometallic Chemistry, 13 (1999) 329-336).*

(Continued)

*Primary Examiner* — Kuo-Liang Peng
(74) *Attorney, Agent, or Firm* — Brinks Gilson & Lione

(57) ABSTRACT

Polybranched organic/inorganic hybrid polymer and method for its manufacture. The hybrid polymer has the form of an inorganic core carrying organic branches. The core is first prepared by controlled hydrolysis and condensation of a silane with a structure: X—B—Si(—Y)$_3$ in which X=NR$_1$R$_2$, while R$_1$, R$_2$ are chosen among hydrogen, alkyl and aryl, or R$_1$, R$_2$ are chosen among condensation products, addition products of one or more type of chemical substances such as acids, alcohols, phenols, amines, aldehydes or epoxides. B is a linkage group chosen among alkylene and arylene which may include oxygen, nitrogen, sulphur, phosphorous, silicon and boron. Y is chosen among hydrolyzable residues such as alkoxy, carboxyl, and halogen. The organic branches are developed by substituting N—H hydrogen atoms in the X—B group by reactions that are typical for primary and secondary amines, and/or by adding an acid that causes an addition to the N atoms of the X—B group in the core. Specific uses of the hybrid polymers are also indicated.

20 Claims, No Drawings

(56) References Cited

OTHER PUBLICATIONS

Gravel et al., Applied Organometallic Chemistry, 13 (1999) pp. 329-336.
A. Sunder, R. Hanselmann, H. Frey, R. Mullhaupt. "Macromolecules", 1998, 32, 4240.
J.P. Majoral, A.M. Caminade and R. Kraemer, "Anales de Quimica Int. Ed", 1997, 93, 415-421.
C. Sanchez. GJ de A.A. Soler-Illia, F. Ribot, T. Lalot, C.R. Mayer, V. Cabuil, "Chem Mater", 2001, 13, 3066.
JP 56-156290 English Abstract, 1 pg.
JP 06-128379 English Abstract, 1 pg.
JP 2001-192485 English translation of Abstract and claims, 3 pgs.
SE 9603174 English Abstract, 1 pg.
WO 2003/029361 A1, Espacenet English translation of description and claims, 28 pgs.

* cited by examiner

METHOD FOR THE MANUFACTURE OF POLYBRANCHED ORGANIC/INORGANIC HYBRID POLYMERS

This application is a divisional of application Ser. No. 11/578,470 filed on May 25, 2007, which is a 371 of PCT/NO2005/000126 filed Apr. 15, 2005 which claims priority from Norwegian Patent Application 20041546 filed Apr. 15, 2004, the entire contents of which are incorporated herein by reference.

The present invention concerns the manufacture of polybranched organic, inorganic hybrid polymers as defined by the preamble of claim 1. According to another aspect the invention concerns a modification of the result of a sol gel process based on at least partially hydrolysed amino silanes manufactured by controlled hydrolysis and condensation of a silane as defined by the preamble of claim 11. According to yet another aspect the invention concerns such polybranched organic/inorganic hybrid polymers as mentioned above. Finally the invention concerns use of such polybranched organic/inorganic hybrid polymers.

BACKGROUND

Polymer materials are utilized in an increasing number of categories of products, such as components for cars, boats, airplanes, within the electronics industry and other advanced industry as well as in paints and other coatings, for special packaging etc. The uses of polymer materials in new categories of products are only limited by the product properties. It is thus a continuous need for development of polymer products with improved properties e.g. with respect to increased scratch resistance, improved weather resistance, increased UV resistance, increased chemical resistance and improved properties with respect to antioxidation, anticorrosion etc.

In addition to pure polymer materials there has also been developed products based on materials that may be described as hybrids between inorganic and organic materials, which means that these materials are macro molecules that may have an inorganic core and organic branches.

Organic polymer molecules with branched structures have an enormous economical growth potential, particularly as components in new materials. So-called dendrimers are important examples of such polymer molecules with a perfectly branched structure as well as hyperbranched polymers with statistically progressive branching. Both dendrimers and hyperbranched polymers are denoted dendritic polymers. Dendritic (from Greec: "dendron"=tree) characterizes the principle of a progressive branching that is more or less perfect (G. R Newkome, C. N. Moorefield, F. Vögtle, "Dendrimers and Dendrons: Concepts. Syntheses. Applications". Wiley-VCH, Weinheim, (2001)). Formula 1 illustrates the principle difference between linear polymers and dendritic polymers (hyperbranched polymers and dendrimers).

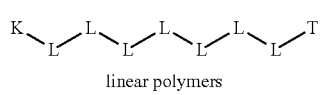

linear polymers

Formula 1

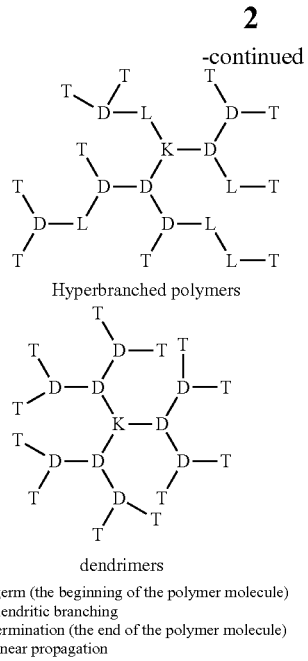

Hyperbranched polymers dendrimers

K = germ (the beginning of the polymer molecule)
D = dendritic branching
T = termination (the end of the polymer molecule)
L = linear propagation Dendritic polymers are particularly interesting because the T units may carry functional groups and the density of available functional groups per weight or volume unit of the polymer is much higher than what is the case for linear polymers. Functional T groups may be used to impart a function in a material, like an antioxidant, a UV absorber, or a radical scavenger as described in WO publication No. 02092668.

Alternatively the T groups may be used as very efficient cross-linkers of organic materials like epoxy resins or polyurethanes or as cross-linkers for thermoplastics. Due to the high degree of cross-linking between dendritic polymers and such organic compounds the dendritic polymers are superior cross-linkers compared to conventional cross-linkers like polyamines, polyalcohols, or multifunctional acrylates. Higher degree of cross-linking of an organic material like a cross-linked thermoplastic improves properties such as chemical resistance, weather resistance and wears resistance and makes the material useful for applications at higher temperature. (Hans Zweifel (ed.), Plastics Additives Handbook, Carl Hanser Verlag, München, (2001), 725-811). The T groups may also be used to organize the dendritic polymers in a network. As component in a material the dendritic polymer thus may induce improved barrier properties. Alternatively such dendritic polymers may be used as a binder or as a component in a thermoset plastic.

Dendrimers are usually manufactured in relatively complicated and expensive synthesis comprising several steps. The process conditions must be maintained very accurately in order to achieve a perfect progressive branch structure. Their industrial applications are therefore limited.

A general way of manufacture of hyper branched polymers was early described by Flory (P. J. Flory, Principles of Polymer Chemistry, Cornell University, (1953)). The polymerization of an $AB_2$ monomer where A may react with B but where the reactions between A and A and between B and B are precluded, leads to a hyperbranched polymer.

Another way of manufacturing hyperbranched polymers involves the utilization of a reactive monomer that also carries an initiator, a so-called "inimer". One example is the base catalyzed reaction between the inimer glycidol and the germ trimethylol propane as illustrated by Formula 2.

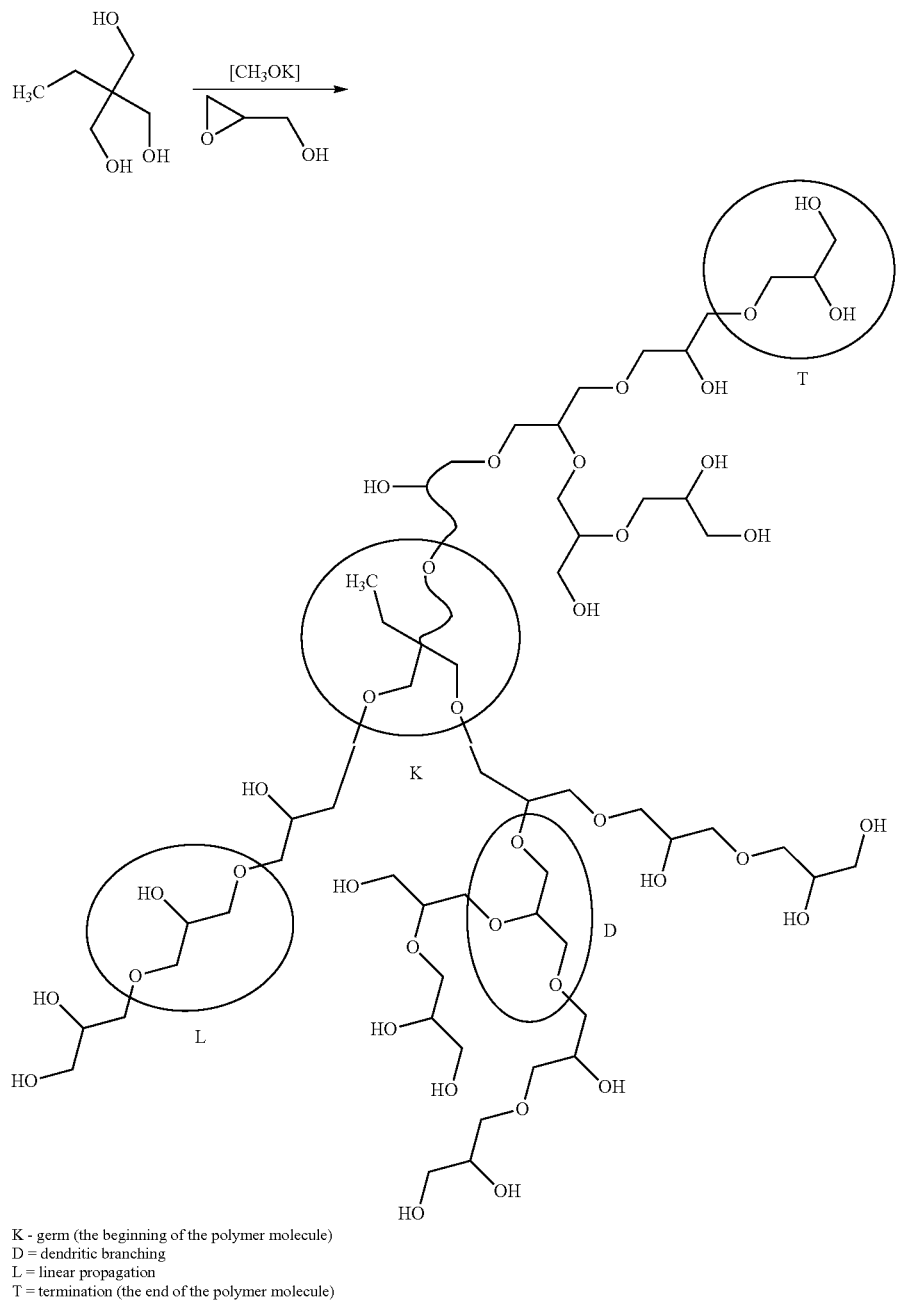

Formula 2

K - germ (the beginning of the polymer molecule)
D = dendritic branching
L = linear propagation
T = termination (the end of the polymer molecule)

Hyperbranched polymers made in this way have properties that are quite similar to corresponding dendrimers (A. Sunder, R. Hanselmann, H. Frey, R. Mühlhaupt; *Macromolecules*, (1998), 32, 4240). This implies a much lower viscosity than that of linear polymers with a comparable number of free available HO-groups. A characteristic feature in the manufacturing process is that the inimer glycidol must be added very slowly to the germ and in a very thin dilution. Thus, the cost-efficiency of the process is severely reduced which is why the utility of hyperbranched polymers in industrial applications is quite limited.

It is previously known to perform certain modifications of the T groups of hyperbranched polymers. J.-P. Majoral, A.-M. Caminade and R. Kraemer, *Anales de Quimica Int Ed.*, (1997), 93, 415-421 describe the functionalization of dendrimers containing phosphorus. The functionalization of the T groups can be made with identical/similar chemical groups or with different chemical groups.

FR 2761691 discusses dendrimers with functional groups at the surface that are modified through a reaction with cyclic thioesters. The reaction leads to a dendrimer surface with thiol groups that are attached to the dendrimer by amide or amine bondings. The products may be used as antioxidants. The dendrimers described are of the type polyamidoamine dendrimers (PAMAM dendrimers). PAMAM dendrimers contain tertiary amines that comparatively easy may be degraded after conversion to quaternary ammonium salts or aminoxides (A. W. Hofmann, *Justus Liebigs Ann. Chem.*

(1851), 78, 253-286; A. C. Cope, E. R. Trumbull, *Org. React.* (1960), 11, 3 17-493; A. C. Cope, T. T. Foster, p. H. Towle, *J. Am. Chem. Soc.* (1949), 71, 3929-3935). Quaternary ammonium salts or aminoxides from amine based dendrimers can be formed when additives of amine based dendrimers are incorporated/compounded into thermoplastics with subsequent processing of the thermoplastics (e.g. film blowing, extrusion, casting). Such a degradation on one hand leads to a partial deterioration of the dendrimer core and on the other hand to formation of degradation products which may leak out and thereby reduce the surface quality of the polymer product. In addition tertiary amines may during processing of the thermoplastic form free radicals by decomposition of hydro peroxides (A. V. Tobolsky, R. B. Mesrobian, *Organic Peroxides*, (1954), Interscience Publishers, New York, p. 104-106). Dendrimers and hyperbranched polymers that contain tertiary amines thereby may induce an unintended degradation of thermoplastics during their processing, storage or use.

WO 01/48057 discusses multifunctional stabilizers against thermal oxidative degradation based on a core structure containing tertiary amines. As mentioned above this may lead to an unintended degradation of the core structure during processing, storage or use of (the) thermoplastics. The molar weight of a typical stabilizer manufactured in accordance with WO 01/48057 is 1246 g/mole.

WO 97/19987 discusses combinations of polymer additives and modified dendrimers that may be used in polymer materials. In the exemplification of WO 97/199987 the dendrimers are based on polypropyleneimine (PPI) of $3^{rd}$, $4^{th}$ and $5^{th}$ generation thereby including 16, 32, and 64 terminal amine groups. The core structure contains tertiary amines which may lead to an unintended degradation of the core structure during processing, storage or use of thermoplastics. The modification of the PPI dendrimer with a fatty acid to form a multifunctional fatty acid amide may bee conducted by means of heating in a suitable solvent. The tertiary amine groups in the core structure of the dendrimer and primary amine groups at the dendrimer surface may in presence of oxygen contribute to partial degradation of the dendrimer structure. As explained above free radicals may be formed by decomposition of hydro peroxides. Such a partial degradation is indicated by a faint brown or yellow colour of the modified PPI dendrimer, like in examples I, XI, and XII in WO 97/19987. Typical molecule weights for modified PPI dendrimers in WO 97/19987 are in the range 10 000 to 40 000 g/mole. In WO 02/092668 surface activated hyperbranched or dendritic stabilizers comprising at least one additive group and a hyperbranched or dendritic core is discussed. In the exemplification of WO 02/092668 only dendritic cores based on 2,2-bis-(hydroxymethyl)-propionic acid is used. The dendritic core and the bonding to the additive group thereby are mainly based on ester bondings, which make the stabilizer sensitive to hydrolysis. In addition the exemplification of WO 02/092668 shows that the molecules of the prepared stabilizers as determined by gel permeation chromatography is between 1000 and 1500 grams/mole.

One type of particulate polymers with properties corresponding to the properties of hyperbranched polymers comprises an inorganic $Si_xO_{(1.5)x}$-core with one T group per Si atom and is known as POSS (polyhedral oligosilesquioxanes). The most common compound of this class is a POSS with x=8 and substantially cubic structure (C. Sanchez, G. J. de A. A. Soler-Illia, F. Ribot, T. Lalot, C. R. Mayer, V. Cabuil; *Chem. Mater.*, (2001), 13, 3066). The manufacture of POSS is expensive (M. C. Gravel, C. Zhang, M. Dinderman, R. M. Laine; *Appl. Organometal. Chem.*, (1999), 13, 329-336 and WO 01/10871) and their industrial applicability is therefore limited. Another type of particulate polymers with properties corresponding to the properties of hyperbranched polymers consists of an inorganic $Si_xO_{(1.5)x}$ core that carries one T group per Si atom and may be manufactured in a sol-gel process through controlled hydrolysis and condensation of a silane with a structure:

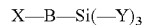

Where Y is chosen among hydrolysable residues and X—B basically corresponds to the T group. The process is described e.g. in Applicant's own WO publication No. 0208343. Sol-gel processes may be cost efficient so that they may be conducted in industrial scale from favourable raw materials and under mild conditions, i.e. without use of high pressures or high temperatures and without particular precautions like extreme dilution or the like. Thus particulate polymers with properties corresponding to properties of hyperbranched polymers manufactured by sol gel processes are industrially applicable in many areas.

Many examples of utilization of sol gel products in polymer products are known (DE 199 33 098, EP 666 290). Normally the main focus is placed upon the inorganic $Si_xO_{(1.5)x}$ core with a size in the nanometer range and thereby upon the sol-gel product as inorganic nano particle, cf. DE 199 33 098 and EP 486 469. The inorganic residues X—B are typically used to anchor the sol gel products in an organic matrix, cf. EP 486 469. The sol gel process involving hydrolysis and condensation of a silane in which the X—B group contains one or more amide groups is particularly simple because no external catalyst is needed and because the process may be conducted at ambient temperature or under moderate heating. One example is controlled hydrolysis and condensation of γ-aminopropyl trialkoxysilane as described in applicant's own patent application, WO publication No. 0208343. Controlled hydrolysis and condensation of silanes in which the X—B groups contains one or more amide groups typically leads to a sol in which the resulting particulate polymer product has an organic/inorganic structure (hybrid polymer) that is comparable with a hyperbranched polymer product with a number of more or less free amine groups in the T groups. Such organic/inorganic hybrid polymers exhibits a large number of functional T groups compared to their weight and/or volume. At the same time its compact structure compared to the structure of linear polymers ensures desirable properties like low viscosity and good admixing properties with thermoset plastics and thermoplastics. An example of an organic/inorganic hybrid polymer with properties corresponding to a hyperbranched polymer is shown by Formula 3.

Formula 3

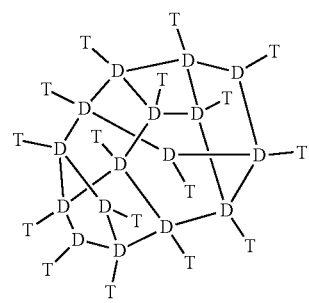

D = dendritic branching based on $SiO_{1.5}$
T = termination (functional T-groups)
D = groups that are bonded to fewer than three D units do not carry hydrolysed and/or condensed substituents.

Organic/inorganic hybrid polymers with properties corresponding to properties of hyperbranched polymers find utilization e.g. as additives for polymer products like thermoset plastics and in lacquers and other types of coatings for surface protection. Used in appropriate amounts and with convenient particle size such hybrid polymers may contribute to a significant improvement of the properties of the plastic material or the lacquer in question, hereunder an increased wear resistance/scratch resistance and/or weather resistance.

Prior art technology in the area sol gel processes/products may broadly be divided in four main categories as elaborated in more detail below, with reference to some examples or publications.

A first category concerns modification of non-hydrolysed amine containing silanes (DE 2023968, WO 03/029361, EP 0253770, EP 666290), commonly with bi-functional epoxy compounds (like e.g. JP 2001192485), and use of same in thermoplastics or in coatings. Hydrolysis and condensation are in some cases subsequently conducted but prior to its addition to the thermoplastics or coating in question. In general this method leads to an undefined distribution of molecular sizes with many large molecules. This implies that a subsequent hydrolysis is difficult to conduct with great success, since water will not reach all sites of the very large molecules. A low degree of hydrolysis implies a lower scratch resistance and a lower weather resistance for the product. A further disadvantage is that the water used for the hydrolysis in presence of the organic parts of the molecule may react in an undesired manner with active groups of said organic parts. Utilization of non-hydrolysed alkoxysilane compounds in a thermoplastic or thermoset plastic material implies that alcohols like ethanol and methanol are formed during the subsequent, slow hydrolysis of the silane compound, i.e. subsequent to the plastic material having been exposed to water. This may lead to reduced mechanical properties of the thermoplastic or the coating. In addition the formation of alcohols such as ethanol and/or methanol may cause migration of additives and/or degradation products to the surface of a thermoplastic or a coating, which may reduce the surface quality severely.

Another category of prior art methods concerns modification of nitrogen containing sol gel products by chemical reactions in which amine groups are not directly involved (S. kar, P. Joly, M. Granier, O. Melnyk, J.-O. Durand, *Eur. J. Org. Chem.*; (2003), 4132-4139) or are not important (U.S. Pat. No. 5,744,243). The latter publication describes a coating composition that is achieved by mixing a) an acid catalysed hydrolysis and condensation of silane and monomer and b) a polymerized solution of organic polymer that contains functions which are compatible with the silane monomer. The coating is used for light reflection.

A third category concerns surface modification solely with $SiO_2$ particles, i.e. particles of silica that may be, but need not be, manufactured by a sol gel process. A (non hydrolysed) silane is typically used for their modification, since the silanes form organic branches on the particles. This type of modification does not involve amine groups as reactive centres for the modification. Patent application No. 9603174-5 describes an aqueous dispersion of silica particles in different polymers used e.g. to increase the hardness.

WO publications Nos. 9407948 and 00/22039 describe this known technology where a surface modification of the oxide particles is conducted by silanization. In some cases the oxide particles may be made of hydrolysed silane. The silanes used for surface modification are not hydrolysed. These particles are used as filler and for the modification of polymers and foils. A disadvantage of products with such particles is that they cannot melt after being cured and their use as hyperbranched polymers is therefore limited. A disadvantage of this technology is that each silane has several functional groups that not necessarily bond to one and the same particle. If or when a silane is bonded to different particles, this contributes to an agglomeration of particles which is unfavourable. This may take place right away or occur over time, which means that the system is unstable. Due to the size of the silanes not many functions may be attached to each particles, which means that the degree of hyper branching is relatively low. In EP 0786499 is described a composition that may be cured in presence of moisture and comprising a) a multi functional acrylate, b) at least one alkoxy-functional organometallic component (TEOS) or hydrolysate, and c) at least one trialkoxyaminosilane.

A fourth category of prior art technology is sol gel processes that is based on hydrolysed silane and where a modification is made by means f an organic monomer, prepolymer or polymer.

EP 486 469 describes an inorganic/organic hybrid polymer that is prepared by polymerizing an organic monomer in presence of a partially or completely hydrolysed silane based sol. A typical example from EP 486 469 is the polymerization of methylmetakrylate in presence of a sol that is prepared by use of metakryloxypropyltrimethoxysilane. Use of the resulting composition is said to be as a wear resistant coating.

In U.S. Pat. No. 5,674,941 a coating composition is described which comprises hydrolysate/condensate of a) an epoxid containing silane, b) an organic amino functional silane, c a copolymer of two components selected from an acrylate monomer, an epoxy monomer, an organosilane and/or a terpolymer of said three components, d) a curing catalyst, e) a multifunctional acrylate, and f) a radical polymerization initiator. The composition is very complex and a chemical substitution of amine groups to form a polybranched, organic/inorganic hybrid polymer is not described.

U.S. Pat. No. 5,096,942 concerns a process in which firstly a polymer based on a hydrolysed silane, a so-called inorganic core, is prepared, which is bonded to a polymer chain like polystyrene. The hydrolysis of the silane is conducted in a way so that the condensation between Si—OH groups is actually prevented. The hydrolysed silane is thereafter added to a hydrolysed metal oxide or silane which results in a organic/inorganic hybrid polymer with properties corresponding to a hyperbranched polymer with a mole weight 1000-100 000 grams/mole. The silane does not contain nitrogen and no deliberate substitution of free amine groups in the sol is mentioned in U.S. Pat. No. 5,096,942.

U.S. Pat. No. 5,110,863 describes the manufacture of a sol that comprises an organosilane (with imidazole) and a metalalkoxide which is hydrolysed and can form an independent coating.

Objects

It is an object of the present invention to provide a method for the manufacture of components, materials, additives and/or material compositions based on particulate, polybranched organic/inorganic hybrid polymers.

It is a further object of the invention to provide methods as defined above in which the organic part may be varied by simple chemical substitutions.

It is a still further object of the invention to make such variation that at least one property of such components, materials, additives and/or material compositions is adjusted, such as but not limited to weather resistance, scratch resistance, barrier properties, dependent upon the actual area of utilization.

The Invention

The above mentioned objects are achieved by a method as defined in claim 1. According to another aspect the present invention concerns a method as defined by claim 2.

According to a further aspect the present invention concerns a particulate polybranched organic/inorganic hybrid polymer as defined by claim 21.

According to further aspects the invention concerns uses of products as manufactured by the methods defined above, as defined by the claims 25-29.

Preferred embodiments of the different aspects of the invention are disclosed by the dependent claims.

A skilled artisan will readily understand that claims 1 and 2 represent two aspects of the same invention and that the sole difference between the two relates to whether the organic amino-functional silanes used are hydrolysed and condensed or not hydrolysed. In the latter case hydrolysis and condensation form the first step in a process comprising at least two steps. In the fox inter case such a step obviously is redundant and therefore omitted. The skilled artisan will furthermore understand that the group X—B is chosen such that it will not be hydrolysed under the conditions that will be applied for the method.

In either case free amine groups are modified through a chemical substitution after the completed silane hydrolysis and condensation. Suitable chemical substitutions are conducted between the free amine groups in the T groups and reactive compounds that preferably react actually quantitatively with more or less free amine groups at temperatures typically below 470 K and pressures typically lower than 0.3 MPa.

Particularly interesting are sol-gel processes by which the T groups may be chemically modified in one or more steps immediately after the hydrolysis and condensation has been completed and for which the reactor equipment used for the silane hydrolysis and condensation may be employed. Such batch processes form the basis for a very cost efficient manufacture of particulate organic/inorganic polybranched polymers which can carry a large number of different T groups and which therefore may be used in a large number of different industrial areas of application.

By reactions typical for primary and secondary amines is meant addition reactions, substitution reactions and combinations of such reactions with suitable reactant such as, but not limited to, compounds comprising epoxy groups, isocyanate groups, reactive double bonds, substitutable groups, and proton donating groups.

By controlled hydrolysis and condensation is herein meant hydrolysis and condensation of a suitable silane compound:

The first step is hydrolysis of a suitable silane compound, R'—Si(OR)$_n$, wherein the group R' does not participate in the hydrolysis or condensation reactions. Alkoxide ligands are replaced by hydroxyl groups:

Si—OR+H—OH Si—OH+ROH

A controlled amount of water and a controlled amount of a glycol based solvent is added during this step. The reaction temperature and the reaction time are also controlled.

The second step is condensation in which the hydroxyl group can react with hydroxyl groups or alkoxy groups from other silicon centres and form Si—O—Si bonds and water or alcohol respectively:

Si—OH+HO—Si Si—O—Si+H$_2$O or

Si—OR+HO—Si Si—O—Si+ROH

To manufacture particles of a certain size it is required to establish chemical conditions that ensures a correct balance between the kinetics of the two reactions, namely condensation and hydrolysis. While the condensation contributes to formation of polymer chains from (single) monomer molecules, the hydrolysis contributes to a polycrystallinic precipitation or oxohydroxide precipitation. The combination of amino-functional silanes and exchange of alkoxide groups with strong ligands will moderate the hydrolysis reaction, which will ensure that the polymer chains not become too long but remain in the size of oligomers. In practice the particles will be prepared with a size of few nanometers, more typically less than 10 nm. A suitable stabilizer is normally added to the reaction composition to avoid oxidative degradation of reactants and reaction products during hydrolysis and condensation and subsequent modification. The resulting solution is comprised of inorganic polymer particles dipersed in a solvent.

THE INVENTION IN FURTHER DETAIL/PREFERRED EMBODIMENTS

According to the present invention a polybranched organic/inorganic hybrid polymer is manufactured by a sol-gel process comprising at least two steps in a defined chronological sequence.

In the first steps the core is prepared by controlled hydrolysis and condensation of a silane with formula:

X—B—Si(—Y)$_3$ with the provisions and definitions stated in claim 1.

In at least one subsequent step branches are developed by:
i) when at least one of R$_1$, R$_2$ is H, adding at least one reactant that is capable of causing N—H hydrogen atoms in the X—B group to be replaced through reactions that are typical for primary and secondary amines, and/or
ii) adding an acid that is capable of causing an addition to N atoms in the X—B group of the core so that the N atoms entirely or partially are converted to quaternary nitronium ions.

The acid used in step ii) may be a Broensted acid or a Lewis acid.

Characteristic and preferred reactions in step i) are addition reactions and substitution reactions or a combination of at least one addition reaction and at least one substitution reaction.

In such reaction reactive compounds that may be used comprises, but are not limited to, epoxides, cyclic and non-cyclic acid derivatives, blocked and non-blocked isocyanates, compounds with reactive double bonds, aldehydes, ketones, and proton donating compounds.

Particularly in substitution reactions compounds R—X comprising a) a suitable atom or atom group X and b) a group R may be used,
in which R—X may react with more or less free amine groups in a substitution reaction in which an atom or an atom group X is replaced by an amine group (Endre Berner, "Lærebok i organisk kjemi", Asehehoug & Co., Oslo (1964), s. 144-147) and where the group R is chosen among non-substituted saturated or unsaturated C$_1$-C$_{24}$ alkyl, substituted saturated or unsaturated C$_1$-C$_{24}$ alkyl, non-substituted or substituted aryl, aliphatic or aromatic carbonyl, while the carbon chains of said compounds optionally can contain one or more of the elements oxygen, nitrogen, sulphur, phosphorous, silicon, and boron; or groups chosen among condensation products or addition products of one or more types of chemical compounds such as acids, alcohols, phenols, amines, aldehydes, or epoxides in which the atom or atom group X preferably is chosen among halogen, substituted or non-substituted alkoxyl, phenoxyl, amine, carboxylate, sulphonate, sulphinate, phosphonate, or phosphinate.

When step i) is an addition reaction it is convenient and preferred that this is conducted by substitution of the N—H hydrogen atom with an A-=B double bond where A, B are chosen among the elements C, O, N, S and P. According to an also preferred alternative the addition reaction involves ring opening of an epoxide group that optionally may be succeeded by reaction (substitution) with a ketone or an aldehyde. Yet another preferred embodiment for the accomplishment of the addition reaction consists in a reaction at the N—H hydrogen atom with a blocked or unblocked isocyanate. Still another preferred embodiment for accomplishing the addition reaction includes ring opening of a cyclic acid anhydride or derivative thereof, such as a carbonic acid derivative. Also a combination of such reactant as mentioned above may be used for the desired addition reaction.

For such an addition reaction a molar excess of reactant may if desired be added to allow repeated addition reactions that in practice leads to a polymerization of the organic branches.

It is preferred to use, as reactant for the alternative of at least one substitution reaction in step i), a mono functional carboxyl acid or a derivative of a sulphinic acid or sulphonic acid.

In step ii) the acid to be used may be a Lewis acid or a Broensted acid.

The method according to the invention is not dependent upon a certain type of reaction medium and may be conducted in both aqueous and organic based dispersion agents. It is particularly surprising and beneficial that it is also applicable in water based media, which is also environmentally favourable.

For some purposes it is preferred to use particularly selected reactants that lead to specific properties for the particulate, polybranched, organic/inorganic hybrid polymer. For example, in order to obtain a product with flame retardant properties it is advantageous to use reactants that comprise halogen for the reaction exemplified as addition reaction or substitution reaction. If a particularly hydrophobic end product is desired it may be advantageous to use at least one fluorinated reactant in step i) and/or ii) of the method according to the invention.

For further use or treatment of the particulate, polybranched organic/inorganic hybrid polymer it is convenient that it has at least one polymerizable double bond, such as part of an acryl group, vinyl group or an unsaturated fatty acid.

Below the choice of reactants and reaction conditions are elaborated in further detail through exemplification of reactants and reaction conditions and by way of reference to conducted experiments.

Examples of stable epoxides for an addition reaction are monoglycidyl compounds that may be represented by:

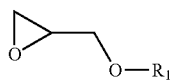

where $R_1$ is chosen among groups like hydrogen, non-substituted saturated or unsaturated $C_1$-$C_{24}$ alkyl, substituted saturated or unsaturated $C_1$-$C_{24}$ alkyl, substituted or non-substituted aryl, aliphatic or aromatic carbonyl, in which the carbon chains of said compounds optionally may contain one or more of the elements oxygen, nitrogen, sulphur, phosphorous, silicon, and boron or where $R_1$ is chosen from condensation products or addition products of one or more type of chemical compounds such as acids, alcohols, phenols, amines, aldehydes or epoxides.

Examples of suitable epoxides include compounds with epoxidized C=C double bonds that may be represented by:

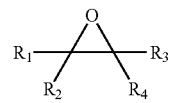

where $R_1$-$R_4$ are chosen among groups like hydrogen, non-substituted saturated or unsaturated $C_1$-$C_{24}$ alkyl, substituted saturated or unsaturated $C_1$-$C_{24}$ alkyl, substituted or non-substituted aryl, aliphatic or aromatic carbonyl, in which the carbon chains of said compounds optionally may contain one or more of the elements oxygen, nitrogen, sulphur, phosphorous, silicon, and boron or where $R_1$ is chosen from condensation products or addition products of one or more type of chemical compounds such as acids, alcohols, phenols, amines, aldehydes or epoxides.

Examples of reactive double bonds are A=B double bonds where A, B are chosen among the elements C, O, N, S and P.

Examples of acid derivatives are:
Derivatives of carboxylic acids

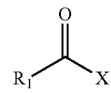

Derivatives of sulphonic acids

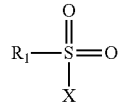

Derivatives of sulphinic acids

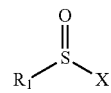

Cyclic acid derivatives
n=0-10
Y=O, S, N—$R_1$

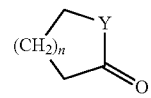

Carbonic acid derivatives

Y=O, S, N—R$_1$, Z=O, S, N—R$_1$

Cyclic acid anhydrides and corresponding derivatives n=1-10

Y=O, S, N—R$_1$

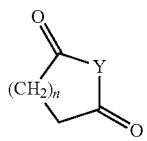

Cyclic carbonic acid derivatives n=1-10

Y=O, S, N—R$_1$, Z=O, S, N—R$_1$

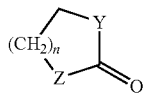

Where R$_1$ is chosen among groups like hydrogen, non-substituted saturated or unsaturated C$_1$-C$_{24}$ alkyl, substituted saturated or unsaturated C$_1$-C$_{24}$ alkyl, substituted or non-substituted aryl, aliphatic or aromatic carbonyl, in which the carbon chains of said compounds optionally may contain one or more of the elements oxygen, nitrogen, sulphur, phosphorous, silicon, and boron or where R$_1$ is chosen from condensation products or addition products of one or more type of chemical compounds such as acids, alcohols, phenols, amines, aldehydes or epoxides and X is an exit group such as halogen, substituted or non-substituted alkoxy, phenoxy, amine, carboxylate, sulphonate, sulphinate, phosphonate, or phosfinate.

Examples of suitable isocyanates may be represented by:

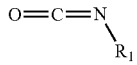

where R$_1$ is chosen among groups like hydrogen, non-substituted saturated or unsaturated C$_1$-C$_{24}$ alkyl, substituted saturated or unsaturated C$_1$-C$_{24}$ alkyl, substituted or non-substituted aryl, aliphatic or aromatic carbonyl, in which the carbon chains of said compounds optionally may contain one or more of the elements oxygen, nitrogen, sulphur, phosphorous, silicon, and boron or where R1 is chosen from condensation products or addition products of one or more type of chemical compounds such as acids, alcohols, phenols, amines, aldehydes or epoxides and where the isocyanate group may be blocked by means of known chemical substances.

Examples of suitable aldehydes and ketones may be represented by:

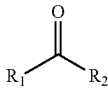

Where R$_1$ is chosen among groups like hydrogen, non-substituted saturated or unsaturated C$_1$-C$_{24}$ alkyl, substituted saturated or unsaturated C$_1$-C$_{24}$ alkyl, substituted or non-substituted aryl, aliphatic or aromatic carbonyl, in which the carbon chains of said compounds optionally may contain one or more of the elements oxygen, nitrogen, sulphur, phosphorous, silicon, and boron or where R$_1$ is chosen from condensation products or addition products of one or more type of chemical compounds such as acids, alcohols, phenols, amines, aldehydes or epoxides.

An example of a combination of reactions is
a) substitution of N—H hydrogen atoms at the non-hydrolyzable substituent X—B group by an epoxide, resulting in formation of an aminoalcohol,
b) substitution of the aminoalcohol by a ketone or an aldehyde under formation, of an oxazolidine.

In the manufacture of a polybranched, organic/inorganic hybrid polymer by a sol-gel process, the hybrid polymer having the form of an inorganic core and organic branches, a suitable stabilizer is normally added to the reaction composition to prevent oxidative degradation of the reactants and reaction products during hydrolysis and condensation and subsequent modification of X—B—Si(—Y)$_3$. Suitable stabilizers are radical scavengers based on hindered amities, one or more antioxidants or a combination of same (Hans Zweifel (ed.), Plastics Additives Handbook, Carl Hanser Verlag, München, (2001), 10-19).

By first hydrolysing the molecules that comprises the organic core and thereafter through suitable reaction, addition or addition, attach the organic branches thereto, the method of the present invention thereby provides a particularly high degree of branching and a control of the particle size in the thus produced sol that has never before been achieved. This leads to several advantages. Firstly the hydrolysis may be conducted more completely than what is the case if the particle composition includes some very large particles. Secondly the risk that water used for the hydrolysis to some extent unintentionally reacts with active groups in the organic parts of the molecule is avoided.

The invention thus provide a possibility of manufacturing a large number of differently functionalized organic/inorganic hybrid polymers with properties corresponding to the properties of hyperbranched polymers, through a simple two step batch process under mild conditions (T<470 K and pressure P<0.3 MPa).

Such organic/inorganic hybrid polymers have properties that are comparable with the properties of organic, hyper-branched polymers and may be used for many applications, like functional additives in thermoplastics and thermoset plastics, e.g. as antioxidant, UV absorb or radical scavenger, as cross-binder in thermoplastics and thermoset plastics, as component in adhesives, lacquers and coating products and as functional material in other connections. Used as additive the polybranched hybrid polymers prepared according to the invention contribute to a lasting increase in scratch resistance and weather resistance for the products in which they are used.

Temperature and stability during hydrolysis of the organic/inorganic hybrid polymers according to the invention are better than those of the organic hyperbranched polymers due to stable Si—O bonds in the polymer core and due to the core's compact structure with a very high degree of cross-linking.

Reversible viscosity changes is observed during heating/cooling due to the particulate structure with a stable inorganic core and function carrying organic groups that are bonded to the inorganic core, which is important in connection with the subsequent treatment/processing of products based on the invention.

The choice of method for the manufacture of materials and products according to the invention enables an industrial utilization of the invention in a cost efficient manner. The manufacture of materials and products according to the invention is based on a batch process under mild conditions (T<470 K and pressure P<0.3 MPa) in which the raw materials are chosen among a definite group of inexpensive silanes and bulk chemicals that are used in large quantities in industrial utilizations of polymers.

By convenient choice of raw materials for the method according to the invention, stabilizers, coating forming additives or other additives may be manufactured. Such stabilizers or other additives provide a broader range of applications than what is the case for known, monofunctional stabilizers and may be used in lacquers, paints, thermoset plastics and thermoplastics. By convenient choice of raw materials one may for instance in combination with a suitable polymer achieve an excellent barrier layer for molecules in gas and liquid form, like water, $O_2$, $CO_2$ and hydrocarbons. It is furthermore possible with the method according to the invention to manufacture additives for avoiding leakages of additives and/or degradation products. Correspondingly self-organizing networks may be formed, such as in adhesives or thermo-stable/thermo-reversible networks that find use in functional materials.

EXAMPLES

Experiment 1

Manufacture of a Polybranched Organic/Inorganic Hybrid Polymer by a Sol-Gel Process a) 221.4 g (1.00 mol) γ-aminopropyltriethoxysilane (A-1100, GE Silicones, USA) was placed in a 1000 ml round bottom flask with hose cooler and magnetic stirrer. A mixture of 93.6 g (0.60 moles) butyldiglykol (BDG) and 22.5 g (1.30 moles) water and 1.00 g Tinuvin 123 (Ciba Specialty Chemicals, Switzerland) was added. The mixture was heated in an oil bath at 110° C. under reflux for 45 minutes. Thereafter the volatile reaction products or reactants were removed in a vacuum distillation at the oil bath temperature of 110° C.-160° C. and a vacuum gradient from about 1000 mbar to less than 20 mbar. The distillation was terminated when the pressure in the round bottom flask has reached 20 mbar or less for 10 minutes. Ca. 192 ml distillate was recovered. The reaction product was a clear, uncoloured liquid with a Gardner Color=1 (according to Gardner Color Scale/ASTM D1544)

b) The reaction product from a) was heated to 70° C. to obtain a clear liquid. Then 256.4 g (1.00 moles) of Araldite DY-E (glycidylether of $C_{12}$-$C_{14}$-alcohol, Vantico AG (Huntsman AG), Switzerland) was added and the reaction mixture was held at 70° C. for an hour. A clear product with a Gardner Color=1, having the form of a viscous gel at 20° C. and a non-viscous liquid at 90° C., was obtained.

The distillate in a) comprises insignificant amounts of volatile amine. In a corresponding experiment in which no stabilizer (like e.g. Tinuvin 123) was used during the manufacturing process, the distillate in a) comprises relatively large amounts of the volatile amine products, which mainly is due to degradation of A-1100 during the synthesis.

Experiments 2-6

The manufacture of a polybranched organic/inorganic hybrid polymer by a sol-gel process like under experiment 1, but with use of other epoxide compounds or a mixture of epoxide compounds in step b). The following products were prepared:

| Experiment # | Silane | Epoxide 1 | Epoxide 2 | Gardner-Colour |
|---|---|---|---|---|
| Experiment 1 | A-1100 | Araldite DY-E (512.8 g; 2.00 moles) | — | 1 |
| Experiment 2 | A-1100 | Araldite DY-K (164.2 g; 1.00 moles) | — | 1-2 |
| Experiment 3 | A-1100 | BGE (130.2 g; 1.00 moles) | — | 1 |
| Experiment 4 | A-1100 | BGE (65.1 g; 0.50 moles) | Araldite DY-K (82.1 g; 0.50 moles) | 1 |
| Experiment 5 | A-1100 | BGE (65.1 g; 0.50 moles) | MGE (71.1 g; 0.50 moles) | 1 |
| Experiment 6 | A-1100 | BGE (65.1 g; 0.50 moles) | FGE (77.1 g; 0.50 moles) | 2 |

BGE = tert-butylglycidylether, CAS [7665-72-7], Sigma-Aldrich Norway AS

MGE = Glycidylmethacrylate, CAS [106-91-2], Sigma-Aldrich Norway AS, stabilized with addition of 0.2% antioxidant hydroquinin monomethylether CAS [150-76-5], Sigma-Aldrich Norway AS Araldite DY-K = glycidyl-2-methylphenylether, CAS [2210-79-9], Huntsman AG, Switzerland FGE = furfurylglycidylether, CAS [5380-87-0], Sigma-Aldrich Norway AS All products were viscous gels at 20° C. and non-viscous liquids at 90° C.

Experiment 7

Comparison example to Example 4 in which a bifunctional epoxide is used as epoxide 2:

| Experiment nr. | silane | Epoxide 1 | Epoxide 2 | Gardner-Color |
|---|---|---|---|---|
| Experiment 7 | A-1100 | BGE (65.1 g; 0.50 moles) | Araldite DY-C (128.2 g; 0.50 moles) | 1 |

Araldite DY-C = 1,4-Bis(2,3-epoxypropoxy)-methylcyclohexane, Huntsman AG, Switzerland.

The product was a clear gel that does not become less viscous when heated. At 200° C. the product starts to degrade with no apparent viscositu change.

Experiment 8

Comparison experiment to Experiment 2, in which step b) was conducted prior to step a):

| Experiment nr. | Silane | Epoxide 1 | Epoxide 2 | Gardner-Color |
|---|---|---|---|---|
| Experiment 8 | A-1100 | Araldite DY-K (164.2 g; 1.00 moles) | — | 4-5 |

The product was a clear gel but had much stronger colour than the product of Experiment 2.

Experiment 9

The manufacture of a polybranched, organic/inorganic hybrid polymer by a sol-gel process while also including an UV absorber during the manufacture:
  a) 221.4 g (1.00 moless) of γ-aminopropyltriethoxysilane (A-1100, GE Silicones, USA) was placed in a 1000 ml round bottom flask with hose cooler and magnetic stirrer. A mixture of 93.6 g (0.60 moles) butyldiglykol (BDG) and 22.5 g (1.30 moles) of water and 1.00 g Tinuvin 123 (Ciba Specialty Chemicals, Switzerland) was added. The mixture was heated in an oil bath at 110° C. under reflux for 45 minutes. To the still warm reaction product a heated solution of 12.0 g Cyasorb UV-1164 (Cytec Inc., USA) dissolved in 36 ml toluene, was added. Thereafter the volatile reaction products or reactants were removed in a vacuum distillation at the oil bath temperature of 110° C.-160° C. and a vacuum gradient from about 1000 mbar to less than 20 mbar. The distillation was terminated when the pressure in the round bottom flask has reached 20 mbar or less for 10 minutes. Ca. 226 ml distillate was recovered. The reaction product was a clear liquid with a Gardner color=3 (according to, Gardner color Scale/ASTM D1544).
  b) The reaction product from a) was heated to 70° C. to obtain a clear liquid. Then 512.8 g (1.00 mol) Araldite DY-E (glycidylether of $C_{12}$-$C_{14}$-alcohol, Vantico AG (Huntsman AG), Switzerland was added and the reaction mixture was held at 70° C. for an hour. The obtained product was clear with a Gardner Color=1, which is a viscous gel at 20° C. and a non-viscous liquid at 90° C. AT 20° C. the product after a few hours shows sign of crystallization. The product again became clear and non-viscous when reheated to 70° C..

Experiment 10

Manufacture of polybranched, organic/inorganic hybrid polymer by a sol-gel process followed by a two step modification:
  a) 221.4 g (1.00 mol) of γ-aminopropyltriethoxysilane (A-1100, GE Silicones, USA) is placed in a 1000 ml round bottom flask with hose cooler and magnetic stirrer. A mixture of 93.6 g (0.60 moles) of butyldiglycol (BDG) and 22.5 g (1.30 moles) of water and 1.00 g Tinuvin 123 (Ciba Specialty Chemicals, Switzerland) was added. The mixture was heated in an oil bath at 110° C. under reflux for 45 minutes. Then volatile reaction products or reactants were removed in a vacuum distillation at the oil bath temperature of 110° C.-160° C. and a vacuum gradient from about 1000 mbar to less than 20 mbar. The distillation was terminated when the pressure in the round bottom flask has reached 20 mbar or less for 10 minutes. Ca. 192 ml of distillate was recovered. The reaction product was a clear, uncoloured liquid with a Gardner Color=1 (according to Gardner Color Scale/ASTM D1544).
  b) The reaction product from a) was heated to 70° C. to obtain a clear liquid. Then 130.2 g (1.00 moles) of tert-butylglycidylether was added and the reaction mixture was held at 70° C. for an hour. A solution of 98.1 g (1.00 moles) of cyclohexanone in 100 ml of toluene was added. The reaction mixture was boiled with reflux for 15 minutes and thereafter the volatile reaction products or reactants were removed by vacuum distillation. A clear product with a Gardner color=2 was obtain, having the form of a viscous gel at 20° C. and a non-viscous liquid at 90° C.

Experiment 11

In a manner corresponding to Experiment 10 a polybranched organic/inorganic hybrid polymer with functional groups of the type hindered amine was prepared from triacetoneamine(2,2,6,6-tetramethyl-4-piperidinone, CAS [826-36-8], Sigma-Aldrich Norway AS).

Experiment 12

In a manner corresponding to Experiment 10 a polybranched organic/inorganic hybrid polymer with functional groups of phenolic type was prepared from 3-hydroxybenzaldehyde, CAS [100-83-4], Sigma-Aldrich Norway AS)

Experiment 13

Manufacture of polybranched, organic/inorganic hybrid polymer by a sol-gel process using an ester.
  a) 221.4 g (1.00 mol) of γ-aminopropyltriethoxysilane (A-1100, GE Silicones, USA) was placed in a 1000 ml round bottom flask with hose cooler and magnetic stirrer. A mixture of 93.6 g (0.60 moles) of butyldiglycol (BDG) and 22.5 g (1.30 moles) of water and 1.00 g of the product from Experiment 11 was added. The mixture was heated in an oil bath at 110° C. under reflux for 45 minutes. Then volatile reaction products or reactants were removed in a vacuum distillation at the oil bath temperature of 110° C.-160° C. and a vacuum gradient from about 1000 mbar to less than 20 mbar. The distillation was terminated when the pressure in the round bottom flask has reached 20 mbar or less for 10 minutes. Ca. 192 ml of distillate was recovered. The reaction product was a clear, uncoloured liquid with a Gardner Color=1 (according to. Gardner Color Scale/ASTM D1544).
  b) The reaction product from a) was heated to 70° C. to obtain a clear liquid. Then 136.2 g (1.00 mol) of methylbenzoate (CAS [93-58-3], Sigma-Aldrich Norway AS) and 0.5 g of acetic anhydride (CAS [108-24-7], Sigma-Aldrich Norway AS) in 150 ml toluene was added and the reaction mixture was boiled with reflux for an hour. Then volatile reaction products or reactants were removed in a vacuum distillation. The reaction product was a clear, and had a Gardner color=1, having the form of a viscous gel at 20° C. and a non-viscous liquid at 90° C.

Experiment 14

Manufacture of polybranched, organic/inorganic hybrid polymer by a sol-gel process using an isocyanate.
a) 221.4 g (1.00 mol) of γ-aminopropyltriethoxysilane (A-1100, GE Silicones, USA) was placed in a 1000 ml round bottom flask with hose cooler and magnetic stirrer. A mixture of 93.6 g (0.60 moles) of butyldiglycol (BDG) and 22.5 g (1.30 moles) of water and 1.00 g of the product from Experiment 11 was added. The mixture was heated in an oil bath at 110° C. under reflux for 45 minutes. Then the volatile reaction products or reactants were removed in a vacuum distillation at the oil bath temperature of 110° C.-160° C. and a vacuum gradient from about 1000 mbar to less than 20 mbar. The distillation was terminated when the pressure in the round bottom flask has reached 20 mbar or less for 10 minutes. Ca. 192 ml of distillate was recovered. The reaction product was a clear, uncoloured liquid with a Gardner color=1 (according to. Gardner Color Scale/ASTM D1544).
b) The reaction product from a) was heated to 70° C. to obtain a clear liquid. Then 155.4 g (1.00 mol) of octylisocyanate (CAS [3158-26-7], Sigma-Aldrich Norway AS) was added and the reaction mixture was held at 70° C. for an hour. A product is obtained which is white and waxy at 20° C. and which is a non-viscous liquid with a Gardner Color=1 at 90° C.

Experiment 15

The product from Experiment 5 is applied to a plasma treated polyethylene sheet (Borealis AS, Norway) and cured by heating the sheet with the product applied from Experiment 5 to 160° C. for 2 hours and 80° C. for 16 hours. A continuous coating with a good adhesion to the polyolefinic surface is formed. The coating is not dissolved from the polyolefinic surface when left in xylene in 180 hours at 40° C.

Experiment 16

The products from Experiment 1, 2 and 9 were compounded into a polypropylene homopolymer (HG430MO, Borealis AS) by means of a Clextral specially instrumented double helix extruder. The amount of polybranched, organic/inorganic hybrid polymer was 5% in all cases. The compounded products were injection moulded by means of a Battenfeld-injection moulding apparatus to 2 mm thick sheets. The sheets were homogenous and about as transparent as injection moulded polypropylene homopolymer without any polybranched, organic/inorganic hybrid polymer.

Experiment 17

The viscosity of the product from Experiment 11 was measured in a rheometer of the type Physika MCR 300 at 20° C. og 90° C. The measurements were conducted three times for each sample and the mean value at each temperature was calculated. The result is shown in the table below. For comparison the viscosity of the POSS compound Isooctyl-POSS (cage mixture; Sigma-Aldrich Norway AS, ref.-nr. 560383) was also measured. The table also shows the viscosity values for n-butanol at the same temperatures (Handbook of Chemistry and Physics, CRC Press, 71. ed., (1990-1991)).

| Compound | Viscosity at 20° C. [mPa*s] | Viscosity at 90° C. [mPa*s] |
|---|---|---|
| Experiment 11 | 800 000 | 800 |
| POSS | 16 000 | 200 |
| n-butanol | 3 | ~0.7 |

The relative change in viscosity shown for the result of Experiment 11 (according to the invention) is of a factor 1000 while it for the comparison examples is of a factor 80 (POSS) and less than 5 (n-butanol).

Experiment 18

Manufacture of polybranched, organic/inorganic hybrid polymer by a sol-gel process in a 5 liter reactor.
2824 g (12.8 moles) of γ-aminopropyltriethoxysilane (DYNASYLAN® AMEO, Degussa AG, Germany) was placed in a 5 liter reactor (NORMAG Labor-und Prozesstechnik, Ilmenau, Germany) with temperature controlled heat mantle, stirring assembly, thermometer, dropping funnel, vertical cooler with column head for rapid change between reflux and distillation and vacuum connection (membrane pump). A mixture of 1241 g (7.7 moles) of butyldiglykol (BDG) and 298 g (16.6 moles) of water and 20 mg of (2,2,6,6-tetrametyl-4-piperidinon, CAS [2564-83-2], Sigma-Aldrich Norway AS). The mixture was heated with reflux for 45 minutes. Then volatile reaction products or reactants were removed in a vacuum distillation at the oil bath temperature of 110° C.-160° C. and a vacuum gradient from about 1000 mbar to less than 20 mbar. The distillation was terminated when the pressure in the round bottom flask has reached 20 mbar or less for 10 minutes. Ca. 2690 ml of distillate was recovered. The reaction product was a clear, colourless liquid with Gardner Color=1 (according to Gardner Color Scale/ASTM D1544).

Experiment 19

Manufacture of polybranched, organic/inorganic hybrid polymer by a sol-gel process in a 5 liter reactor.
2801 g (12.7 moles) of γ-aminopropyltriethoxysilane (DYNASYLAN® AMEO, Degussa AG, Germany) was placed in a 5 liter reactor (NORMAG Labor-und Prozesstechnik, Ilmenau, Germany) with temperature controlled heat mantle, stirring assembly, thermometer, dropping funnel, vertical cooler with column head for rapid change between reflux and distillation and vacuum connection (membrane pump). A mixture of 821 g (7.6 moles) of 2-butoxyethanol (DOWANOL EB, Dow Chemical, USA) and 296 g (16.4 moles) of water and 16 mg of the reaction product of Experiment 11. The mixture was heated under reflux for 45 minutes. Then the volatile reaction products or reactants were removed in a vacuum distillation at the oil bath temperature of 110° C.-160° C. and a vacuum gradient from about 1000 mbar to less than 20 mbar. The distillation was terminated when the pressure in the round bottom flask has reached 20 mbar or less for 10 minutes. Ca. 2334 ml of distillate was recovered. The reaction product was a clear, uncoloured liquid with a Gardner Color=1 (according to. Gardner Color Scale/ASTM D1544).

Experiment 20

Development of the organic branches in a polybranched, organic/inorganic hybrid polymer as prepared in Experiment 19.
- a) 558 g of the reaction product from Experiment 19 was heated to 70° C. Then 625 g (4.8 moles) of tert-butylglycidylether (BGE) and the reaction mixture was heated to 100° C. The reaction is strongly exothermic and by means of the controllable heat mantle was ensured that the temperature in the reaction mixture did not exceed 160° C. The reaction mixture was cooled to 80° C.
- b) A hot solution of 621 g triacetoneamine (TAA) in 552 g toluene was added. The reaction mixture was heated under reflux for 20 minutes. Thereafter an azeotrope of toluene and water was distilled off, ca. 610 g. The procedure was terminated with vacuum distillation at 20 mbar or less and a temperature in the reaction mixture of 160° C. A brownish, yet clear product was obtained which was a viscous gel at 20° C. and a non-viscous liquid at 90° C.

Experiment 21

Development of the organic branches in a polybranched, organic/inorganic hybrid polymer as prepared in Experiment 19.
- a) 551 g of the reaction product from Experiment 19 was heated to 70° C. Then 1460 g (5.7 moles) of Araldite DY-E (glycidylether of $C_{12}$-$C_4$-alcohol, Huntsman AG, Switzerland) was added and the reaction mixture was heated to 100° C. The reaction is strongly exothermic and by means of the controllable heat mantle was ensured that the temperature in the reaction mixture did not exceed 160° C. The reaction mixture was cooled to 80° C.
- b) 160 g of a hot solution of Camphor (CAS [76-22-2], Sigma-Aldrich Norway AS) in 280 g hexane was added. The reaction mixture was heated under reflux for 20 minutes. Thereafter an azeotrope of hexane and water was distilled off, ca. 290 g. The procedure was terminated with vacuum distillation at 20 mbar or less and a temperature in the reaction mixture of 160° C. A product was obtained which was a clear viscous gel at 20° C. and a clear non-viscous liquid at 90° C.

Experiment 22

Development of the organic branches in a polybranched, organic/inorganic hybrid polymer as prepared in Experiment 19.

480 g of the reaction product from Experiment 19 was heated to 80° C. Then 1562 g (12.0 moles) of tert-butylglycidylether (BGE) was added and the reaction mixture was heated to 100° C. The reaction is strongly exothermic and by means of the controllable heat mantle was ensured that the temperature in the reaction mixture did not exceed 160° C. The procedure was terminated with vacuum distillation at 20 mbar or less and a temperature in the reaction mixture of 160° C. A brownish, yet clear product was obtained which was a strongly viscous gel at 20° C. and a non-viscous liquid at 140° C.

Experiment 23

Development of the organic branches in a polybranched, organic/inorganic hybrid polymer as prepared in Experiment 19.

140 g of the reaction product from Experiment 19 was heated to 70° C. Then 466 g (4.1 moles) of ε-caprolactone (CAS [502-44-3], Sigma-Aldrich Norway AS) was added and the reaction mixture was heated to 100° C. Two hours later 627 g of Araldite DY-E (glycidylether of $C_{12}$-$C_{14}$-alcohol, Huntsman AG, Switzerland) was added and the reaction mixture was heated to 160° C. The procedure was terminated with vacuum distillation at 20 mbar or less and a temperature in the reaction mixture of 160° C. 420 g of a distillate was distilled out. A clear gel which was viscous at 20° C. and non-viscous (liquid) at 90° C. was obtained.

Experiment 24

Development of the organic branches in a polybranched, organic/inorganic hybrid polymer as prepared in Experiment 19.

70 g of the reaction product from Experiment 19 was heated under agitation in a borosilicate glass flask (Schott AG, Germany) by means of a water bath to 70° C. Then 171 g (1.5 moles) of ε-caprolactone (CAS [502-44-3], Sigma-Aldrich Norway AS) was added and the reaction mixture was heated to 90° C. Two hours later 154 g Araldite DY-E (glycidylether of $C_{12}$-$C_{14}$-alcohol, Huntsman AG, Switzerland) was added and the reaction mixture was held at 90° C. for four hours under agitation. Thereafter the reaction mixture was agitated at 40° C. for a week. A clear gel which was viscous at 20° C. and non-viscous (liquid) at 90° C. was obtained.

Experiment 25

Development of the organic branches in a polybranched, organic/inorganic hybrid polymer as prepared in Experiment 19.

28 g of the reaction product from Experiment 19 was heated under agitation in a borosilicate glass flask (Schott AG, Germany) by means of a water bath to 70° C. Then 137 g (1.5 moles) of ε-caprolactone (CAS [502-44-3], Sigma-Aldrich Norway AS) was added and the reaction mixture was heated to 90° C. Two hours later 57 g oleic acid (CAS [112-80-1], Sigma-Aldrich Norway AS) was added and the reaction mixture was agitated at 40° C. for 16 hours. A clear gel which was viscous at 20° C. and non-viscous (liquid) at 90° C. was obtained.

Experiment 26

Development of the organic branches in a polybranched, organic/inorganic hybrid polymer as prepared in Experiment 19.

35 g of the reaction product from Experiment 19 was placed in a borosilicate glass flask (Schott AG, Germany). Under agitation 31 g propylenecarbonate (Huntsman AG, Switzerland) was added and the reaction mixture was agitated at ambient temperature. The reaction is strongly exothermic and a clear gel which is viscous at 20° C. and non-viscous (liquid) at 120° C. was obtained.

Experiment 27

Development of the organic branches in a polybranched, organic/inorganic hybrid polymer as prepared in Experiment 19.

14.0 g of the reaction product from Experiment 19 was placed in a borosilicate glass flask (Schott AG, Germany). Then 12.3 g propylenecarbonate (Huntsman AG, Switzerland) was added under agitation and the reaction mixture was agitated at ambient temperature. The reaction is strongly exothermic and a clear gel which is viscous at 20° C. and non-viscous (liquid) at 120° C. was obtained. 34,1 of a lacquer (SZ-006, Rhenania GmbH, Germany) was added. The composition was agitated at 40° C. for 40 hours. A modified lacquer was obtained which had approximately the same shelf-life as the original lacquer.

Experiment 28

Development of the organic branches in a polybranched, organic/inorganic hybrid polymer as prepared in Experiment 19.

14 g of the reaction product from Experiment 19 was placed in a borosilicate glass flask (Schott AG, Germany). Then 49 g of Araldite DY-P (p-tert-butylphenylglycidyleter, Huntsman AG, Switzerland) was added under agitation and the reaction mixture was agitated at ambient temperature. The reaction is strongly exothermic and a clear gel which is viscous at 20° C. and non-viscous (liquid) at 120° C. was obtained.

Experiment 29

Development of the organic branches in a polybranched, organic/inorganic hybrid polymer as prepared in Experiment 19.

15.4 g of the reaction product from Experiment 19 was dispersed in 40 g of water and placed in a borosilicate glass flask (Schott AG, Germany). The dispersion was agitated at 40° C. for two hours and thereafter filtered, first through a filter paper and then through a teflon membrane filter (pore size 0.45 μm). The filtrate was placed in another borosilicate flask and heated to 40° C. Then a mixture of 23 g of glycidylmethacrylate and 8 g butoxyethanol was added under agitation. The reaction mixture was agitated at 40° C. for two hours. Then 0.5 g of sodium salt of dodecylbenzenesulphonic acid (CAS [25155-30-0], Sigma-Aldrich Norway AS) was added. A clear dispersion with a very good shelf-life was obtained.

Experiment 30

Manufacture of Polyurethane Foam

Type isocyanate: 4,4'-methylene-bis(phenylisocyanate) 98%, MDI, (CAS [101-68-8], Sigma-Aldrich Norway AS)
Type polyol: Terathane 650 polyetherglycol (CAS [25190-06-1], Sigma-Aldrich Norway AS, produced by DuPont)

| Test | Amount polyol (g) | Amount Isocyanat (g) | Hybrid polymer from exp. 24 | Density (g/cm³) |
|---|---|---|---|---|
| 50412-PU-6 | 19.5 | 7.5 | 0 | 1.079 |
| 50412-PU-7 | 13.5 | 7.5 | 6.0 | 0.790 |

The components were mixed at 60° C. with a stirring assembly run at high speed. In test 50412-PU-6 the sample was stirred some minutes without resulting in a cured sample. In test 50412-PU-7 the sample cured/foamed after a few minutes of stirring.

The samples were post-cured at 80° C. in hot cabinets over night, which led to a curing also of sample 50412-PU-6.

Experiment 31

Molecular Weight Analysis with GPC (Gel Permeational Chromatography or Size Exclusion Chromatography (SEC)

A series of three SEC columns based on 5 μm particles and pore size from 10000 Å til 100 Å were used in addition to a standard pump and a refractive index detector (RID). Cyclohexane or tetrahydrofurane was used as mobile phase and solvent. The molecular weight analysis was based on polystyrene standards. The results for a number of organic/inorganic hybrid polymers according to the present invention are shown in the table below:

Results Base Don Polystyrene as Standard and Cyclohexane as Mobile Phase:

| Navn: | Top 1 Mp: | Top 2 Mp: | Top 3 Mp: | Top 4 Mp: | Top 1 Area % | Top 2 Area % | Top 3 Area % | Top 4 Area % |
|---|---|---|---|---|---|---|---|---|
| Exp. 21 | >1,000,000* | ~6000 | ~1000 | | 7% | 44% | 49% | |
| Exp. 23 | ~6000 | ~3000 | ~1000 | | 48% | 28% | 24% | |
| Exp. 22 | >1,000,000* | ~8000 | ~3000 | ~1000 | 4% | 24% | 43% | 29% |

*Outside the calibration curve

Results Base Don Polystyrene as Standard and Tetrahydrofurane as Mobile Phase:

| Name | Exp. 28 | Exp. 24 |
|---|---|---|
| Top1, Mp: | >1,000,000 | ~8000 |
| Top2, Mp: | 31 000 | ~1000 |
| Top3, Mp: | | ~900 |
| Top4, Mp: | | ~700 |
| Top5, Mp: | | ~600 |
| Top6, Mp: | | ~400 |
| Top1, Area % | | 40 % |
| Top1, Area % | | 29 % |
| Top1, Area % | | 6 % |
| Top1, Area % | | 9 % |
| Top1, Area % | | 9 % |
| Top1, Area % | | 7 % |

* Outside the calibration curve

Experiment 32

PMMA

PMMA (Plexiglass) was treated with $O_2$ plasma for 30 sec (effect 500 W and flux 200 standard $cm^3$/min.).
Manufacture of the Lacquer Exp. 29
Application:
the lacquer was applied plasma treated PMMA by bar coating (rod number 26). Immediately after application the sheet was placed in a hot air oven at 100° C. for 10 minutes. The sheet was then removed from the oven and cooled in air.
Testing:
The adhesion was determined by a standard tape-test. A scratch pattern was made by the use of lattice-cutting test tool from Erichsen (a scratch pattern was made with the lattice-cutting test tool from Erichsen). The tape was applied to the pattern with an even pressure. The tape was removed from the sheet and the surface against adhesive was observed in an optical microscope. The surface had small or no remains of the coating.

Experiment 33

PC

PC (Lexan) was treated with $O_2$ plasma for 30 sec. (effect 500 W and flux 200 standard $cm^3$/min.).
Manufacture of the Lacquer Exp. 29
Application:
The lacquer was applied plasma treated PC by bar coating (rod number 26). Immediately after application the sheet was placed in a hot air oven at 150° C. for 10 minutes. The sheet was then removed and cooled in air.
Testing:
The adhesion was determined by means of a standard tape test. A scratch pattern was made by the use of lattice cutting test tool from Erichsen. The tape was applied to the pattern with an even pressure. The tape was removed from the sheet and the surface against adhesive was observed with an optical microscope. The surface had small or no remains of the coating.

The scratch resistance was tested with a hardness pen from Erichsen, Germany. No scratches were observed when the same force (6N) was used as on an unmodified PC that showed many scratches.

Experiment 34

PP

PP was treated with $O_2$ plasma for 30 sec. (effect 500 W and flux 200 standard $cm^3$/min.).
Manufacture of the Lacquer Exp. 29
Application:
The lacquer was applied plasma treated PP by bar coating (rod number 26). Immediately after application the sheet was placed in a hot air oven 120° C. for 10 min. The sheet was then removed and cooled in air.
Testing:
The adhesion was determined by means of a standard tape test. A scratch pattern was made by the use of lattice-cutting test tool from Erichsen. The tape was applied to the pattern with an even pressure. The tape was removed from the sheet and the surface against adhesive was observed with an optical microscope. The surface had small or no remains of the coating.

Experiment 35

Wood Treatment

Porous wood was treated with the lacquer by brush application of the wood sample in four layers. Immediately after application the wood plate was placed in a hot air oven 80° C. for 120 min. The plate was then removed and cooled in air. The procedure was repeated once.
Testing:
Wetting of the wood sample by water was tested by placing one drop of water on the wood board. The water drop used 2 minutes at room temperature to dissipate into the treated wood while it penetrated untreated tree within 20 seconds.

Impregnation of porous paper: Porous sheets of paper was impregnated with the lacquer and placed in a hot air oven at 80° C. for 120 minutes. The sheet was then removed and cooled in air.
Testing:
Wetting of the impregnated sheet of paper was tested by placing one drop of water on the paper sheet. The water drop remained on top of the paper sheet without being absorbed, while a drop of water immediately was absorbed by an untreated sheet of the paper.

Experiment 36

Application of a Lacquer on Aluminium

Manufacture of the Lacquer Exp. 29
Application:
The lacquer was applied to an aluminium sheet by bar coating (rod number 26). immediately after application the sheet was placed in a hot air oven 250° C. for 5 min. The sheet was then removed and cooled in air.
Testing:
Scratch resistance was tested by use of a hardness pen from Erichsen, Germany. Scratches could be observed when a force more than 2.5 N was used.

The invention claimed is:
1. Method for the preparation of particulate, polybranched organic/inorganic hybrid polymer by a sol-gel process, said hybrid polymer having form of an inorganic core carrying organic branches, wherein the method comprises at least the following two steps in chronological sequence:
A) the core is prepared by controlled hydrolysis and condensation in the presence of water of an amino-functional silane with a structure:

$$X-B-Si(-Y)_3$$

in which $X=NR_1 R_2$, wherein $R_1$, $R_2$ are chosen among hydrogen, saturated or unsaturated $C_1$-$C_{18}$-alkyl, substituted or not substituted aryl, wherein the carbon chains of said silane optionally can include one or more of the elements oxygen, nitrogen, sulphur, phosphorus, silicon and boron, and optionally may include one or more hydrolyzable silane units, or $R_1$, $R_2$ are chosen among condensation products, addition products of one or more type of chemical substances selected from the group consisting of acids, alcohols, phenols, amines, aldehydes or epoxides, B is a linkage group chosen among saturated and unsaturated $C_1$-$C_{18}$-alkylene, substituted or non-substituted arylene in which the carbon chains of said substances optionally may include one or more branching and optionally one or more of the elements oxygen, nitrogen, sulphur, phosphorus, silicon and boron, Y is chosen among hydrolyzable residues selected from the group consisting of alkoxy, carboxyl, and halogen,
  B) the organic branches are developed by:
    i) wherein at least one of $R_1$, $R_2$ is H, adding at least one reactant that is capable of causing N—H hydrogen atoms on the X—B-group in the core to be substituted by substitution reactions, and optionally
    ii) adding an acid that is capable of causing an addition to the N atoms of the X—B group of the core, so that the N atoms totally or partially are converted to quaternary nitronium ions.

2. Method as claimed in claim 1 wherein the substitution reaction involves the reaction with at least one compound R—X' where X' is an atom or an atom group that is substituted by an amine group and where the R group is chosen among non-substituted saturated or unsaturated $C_1$-$C_{24}$-alkyl, substituted saturated or unsaturated $C_1$-$C_{24}$-alkyl, substituted or non-substituted aryl, aliphatic or aromatic carbonyl, while the carbon chains of said compounds may include one or more of the elements oxygen, nitrogen, sulphur, phosphorus, silicon and boron, or groups that are chosen among condensation products or addition products of one or more types of chemical substances selected from the group of acids, alcohols, phenols, amines, aldehydes or epoxides and where the atom or atom group, X' is chosen among halogen, substituted or non-substituted alkoxyl, phenoxyl, amine, carboxylate, sulphonate, sulphinate, phosphonate or phosphinate.

3. Method as claimed in claim 1, wherein the substitution reaction involves reaction of at least one derivative of a mono-functional carboxylic acid.

4. Method as claimed in claim 1, wherein the substitution reaction involves reaction with at least one derivative of a sulphinic acid.

5. Method as claimed in claim 1, characterized in that the acid added under step ii) is a Lewis acid or a Broensted acid.

6. Method as claimed in claim 1, wherein the substitution of N—H hydrogen atoms in step i) is conducted in an aqueous medium.

7. Method as claimed in claim 1, wherein at least one halogenated organic compound is used for the substitution in step i).

8. Method as claimed in claim 1, wherein at least one fluorinated organic compound is used for the substitution in step i) and/or step ii).

9. A composition comprising a particulate, polybranched organic/inorganic hybrid polymer prepared by the method defined by claim 1; and a second component selected from thermoplastics, thermoset plastics, adhesives, lacquers and coatings.

10. Particulate, polybranched organic/inorganic hybrid polymer prepared by the method defined by claim 1, characterized in that the polybranched organic/inorganic hybrid polymer is dispersed or dissolved in an aqueous medium.

11. Particulate, polybranched organic/inorganic hybrid polymer prepared by the method defined by claim 1, characterized in that it comprises at least one polymerizable double bond.

12. Particulate, polybranched organic/inorganic hybrid polymer as claimed in claim 11, characterized in that the polymerizable double bond is part of an acryl group, vinyl group, or of an unsaturated fatty acid.

13. Method as claimed in claim 1, characterized in that substitution of N—H hydrogen atoms in step i) is made by a combination of at least one substitution reaction and at least one addition reaction.

14. Method for preparation of particulate polybranched organic/inorganic hybrid polymer said hybrid polymer having form of an inorganic core carrying organic branches by modifying the result of a sol-gel process based on at least partially hydrolysed, organic amino-functional silanes prepared by controlled hydrolysis and condensation in the presence of water of an amino-functional silane with a structure:

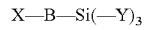

in which X=N $R_1$ $R_2$, wherein $R_1$, $R_2$ is chosen among hydrogen, saturated or unsaturated $C_1$-$C_{18}$-alkyl, substituted or not substituted aryl, wherein the carbon chains of said silane optionally can include one or more of the elements oxygen, nitrogen, sulphur, phosphorus, silicon and boron, and/or optionally may include one or more hydrolyzable silane units, or $R_1$, $R_2$ are chosen among condensation products, addition products of one or more type of chemical substances selected from the group consisting of acids, alcohols, phenols, amines, aldehydes or epoxides, B is a linkage group chosen among saturated and unsaturated $C_1$-$C_{18}$-alkylene, substituted or non-substituted arylene while the carbon chains of said substances optionally may include one or more branching and/or one or more of the elements oxygen, nitrogen, sulphur, phosphorus, silicon and boron, Y is chosen among hydrolyzable residues selected from the group consisting of alkoxy, carboxyl, and halogen while N—H hydrogen atoms in the hybrid polymer subsequent of hydrolysis and condensation are substituted by organic residues, characterized in that the organic branches are made by:
  i) wherein at least one of $R_1$, $R_2$ is H, adding at least one reactant that is capable of causing N—H hydrogen atoms on the X—B-group in the core to be substituted by substitution reactions, and optionally
  (ii) adding an acid that is capable of causing an addition to the N atoms of the X—B group of the core, so that the N atoms totally or partially are converted to quaternary nitronium ions.

15. A composition comprising a particulate, polybranched organic/inorganic hybrid polymer prepared by the method defined by claim 14; and a second component selected from thermoplastics, thermoset plastics, adhesives, lacquers and coatings.

16. Method as claimed in claim 14, wherein the substitution reaction involves the reaction with at least one compound R—X' where X' is an atom or an atom group that is substituted by an amine group and where the R group is chosen among non-substituted saturated or unsaturated $C_1$-$C_{24}$-alkyl, substituted saturated or unsaturated $C_1$-$C_{24}$-alkyl, substituted or non-substituted aryl, aliphatic or aromatic carbonyl, while the carbon chains of said compounds may include one or more of the elements oxygen, nitrogen, sulphur, phosphorus, silicon and boron, or groups that are chosen among condensation products or addition products of one or more types of chemical substances selected from the group of acids, alcohols, phenols, amines, aldehydes or epoxides and where the atom or atom group, X' is chosen among halogen, substituted or non-substituted alkoxyl, phenoxyl, amine, carboxylate, sulphonate, sulphinate, phosphonate or phosphinate.

17. Method as claimed in claim 14, wherein the substitution reaction involves reaction of at least one derivative of a mono-functional carboxylic acid.

18. Method as claimed in claim 14, wherein the substitution reaction involves reaction with at least one derivative of a sulphinic acid.

19. Method as claimed in claim 14, characterized in that the acid added under step ii) is a Lewis acid or a Broensted acid.

20. Method as claimed in claim 14, characterized in that substitution of hydrogen atoms in step i) is made by a combination of at least one substitution reaction and at least one addition reaction.

* * * * *